United States Patent [19]

Zenno et al.

[11] Patent Number: 5,468,631
[45] Date of Patent: Nov. 21, 1995

[54] GENE ENCODING ENZYME HAVING FLAVIN REDUCING ACTIVITY AND NITROREDUCTASE ACTIVITY

[75] Inventors: Shuhei Zenno, Kanagawa; Satoshi Inouye, Tokyo; Hiromasa Kanoh, Kanagawa; Kaoru Saigo, Tokyo, all of Japan

[73] Assignee: Chisso Corporation, Osaka, Japan

[21] Appl. No.: 412,108

[22] Filed: Mar. 28, 1995

Related U.S. Application Data

[63] Continuation of Ser. No. 987,216, Dec. 8, 1992, abandoned.

[30] Foreign Application Priority Data

Dec. 16, 1991 [JP] Japan ................................. 3-351717
Oct. 16, 1992 [JP] Japan ................................. 4-279029

[51] Int. Cl.[6] ........................... C12N 9/02; C12N 1/20; C12P 21/06; C07H 19/00
[52] U.S. Cl. ..................... 435/189; 435/69.1; 435/191; 435/252.3; 435/320.1; 536/22.1; 536/23.1; 536/23.2; 536/23.7
[58] Field of Search ................... 435/69.1, 189, 435/191, 252.3, 320.1; 536/22.1, 23.1, 23.2, 23.7

[56] References Cited

PUBLICATIONS

Journal of Bacteriology, 173, [12], 3673–3679, (1991).
Journal of Bioluminescence and Chemiluminescence, 5, 187–192 (1990).
Applied and Environmental Microbiology, 55, [10], 2607–2612, (1989).
Biochemie, 54, 1197–1204, (1972).
The Journal of Biological Chemistry, 252, [21], 7495–7499, (1977).
Eur. J. Biochem, 57, 461–467, (1975).
Molecular and Cellular Biochemistry 44, 181–187, (1982).
Biochemistry, 16, [13], 2932–2936, (1977).
Anch. Int. Physiol. Biochem, 83, [2], 354–356, (1975).
Journal of Bacteriology, vol. 173, No. 12, Jun. 1991, Baltimore, US pp. 3673–3679, G. Spyrou et al. "Characterization of the flavin reductase gene (fre) of *Escherichia coli* and construction of a pasmid for overproduction of the enzyme".
Journal of Bioluminescence and Chemiluminescene, vol. 5 No. 3, 1990, pp. 187–192, J. T. Lavi et al. "Affinity purification of bacterial luciferase and NAD(P)H:FMN oxidoreductases by FMN–Sepharose for analytical applications".
Journal of Biological Chemistry, vol. 266, No. 7, Mar. 5, 1991, Baltimore, US pp. 4119–4125, C. Bryant et al. "Purification and characterization of an oxygen–insensitive NAD(P)H nitroeductase from *Enterobacter cloacae*".
Biochemistry, vol. 16, No. 13, Jun. 28, 1977, Easton, Pa. U.S. pp. 2932–2936 E. Jablonski et al. "Purification and properties of the NADH and NADH specific FMN oxidoreductases from *Beneckea harveyi*".
Journal of Biological Chemistry, vol. 266, No. 7, Mar. 5, 1991, Baltimore, U.S. pp. 4126–413 C. Bryant et al. "Cloning, nucleotide sequence, and expression of the nitroreductase gene from *Enterbacter cloacae*".
Mutation Research, vol. 216, No. 1, Feb. 1989, NL pp. 211–220 M. Watanabe et al. "A Sensitive method for the detection of mutagenic nitroarenes: construction of nitroreductase–overproducing derivatives of *Salmonella typhimurium* strains TA98 and TA100".
Archives of Biochemistry and Biophysics vol. 193, No. 1, Mar. 1979, New York, U.S. pp. 110–116, S–C TU et al. "Kinetic studies on the mechanism of bacterial NAD(P)H: flavin oxidoreductase".
Nucleic Acids Research vol. 18, No. 4, 1990, London, GB p. 1059, M. Watanabe et al. "Nucleotide sequence of Salmonella typhirmurium nitroreductase gene".

*Primary Examiner*—Robert A. Wax
*Assistant Examiner*—Hyosuk Kim
*Attorney, Agent, or Firm*—Wenderoth, Lind & Ponack

[57] ABSTRACT

The present invention succeeds in isolating a gene encoding an enzyme having an FMN reducing activity and a nitroreductase activity derived from luminous bacteria *Vibrio fischeri* (ATCC 7744), elucidating its primary structure, and producing *Escherichia coli* which can express the gene in large quantities. That is, the present invention provides a gene encoding an enzyme having the flavin reducing activity and the nitro-reductase activity, an enzyme produced therefrom, a recombinant vector containing the gene, and bacteria containing the recombinant vector.

7 Claims, 7 Drawing Sheets

Fig. 1

| | | | | | | | | | | | | | | | |
|---|---|---|---|---|---|---|---|---|---|---|---|---|---|---|---|
| ATG | ACL | CAK | CCL | ATM | ATM | CAK | GAK | XTY | GAJ | AAK | WGZ | TAK | ACL | QRS | AAJ | 48
| Met | Thr | His | Pro | Ile | Ile | His | Asp | Leu | Glu | Asn | Arg | Tyr | Thr | Ser | Lys |
| 1 | | | | 5 | | | | | 10 | | | | | 15 | |
| AAJ | TAK | GAK | CCL | QRS | AAJ | AAJ | GTL | QRS | CAJ | GAJ | GAK | XTY | GCL | GTL | XTY | 96
| Lys | Tyr | Asp | Pro | Ser | Lys | Lys | Val | Ser | Gln | Glu | Asp | Leu | Ala | Val | Leu |
| | | | 20 | | | | | 25 | | | | | 30 | | |
| XTY | GAJ | GCL | XTY | WGZ | XTY | QRS | GCL | QRS | QRS | ATM | AAK | QRS | CAJ | CCL | TGG | 144
| Leu | Glu | Ala | Leu | Arg | Leu | Ser | Ala | Ser | Ser | Ile | Asn | Ser | Gln | Pro | Trp |
| | | 35 | | | | | 40 | | | | | 45 | | | |
| AAJ | TTK | ATM | GTL | ATM | GAJ | QRS | GAK | GCA | GCL | AAJ | CAJ | GGL | ATG | CAK | GAK | 192
| Lys | Phe | Ile | Val | Ile | Glu | Ser | Asp | Ala | Ala | Lys | Gln | Gly | Met | His | Asp |
| | 50 | | | | | 55 | | | | | 60 | | | | |
| QRS | TTK | GCL | AAK | ATG | CAK | CAJ | TTK | AAK | CAJ | CCL | CAK | ATM | AAJ | GCL | TGK | 240
| Ser | Phe | Ala | Asn | Met | His | Gln | Phe | Asn | Gln | Pro | His | Ile | Lys | Ala | Cys |
| 65 | | | | | 70 | | | | | 75 | | | | | 80 |
| QRS | CAK | GTG | ATM | XTY | TTK | GCL | AAK | AAJ | XTY | QRS | TAK | ACL | WGZ | GAK | GAK | 288
| Ser | His | Val | Ile | Leu | Phe | Ala | Asn | Lys | Leu | Ser | Tyr | Thr | Arg | Asp | Asp |
| | | | | 85 | | | | | 90 | | | | | 95 | |
| TAK | GAK | GTG | GTL | XTY | QRS | AAJ | GCL | GTL | GCL | GAK | AAJ | WGZ | ATM | ACL | GAJ | 336
| Tyr | Asp | Val | Val | Leu | Ser | Lys | Ala | Val | Ala | Asp | Lys | Arg | Ile | Thr | Glu

Fig. 2

| | |
|---|---|
| ATG ACG CAT CCA ATT ATT CAT GAT CTT GAA AAT CGT TAT ACA TCA AAA<br>Met Thr His Pro Ile Ile His Asp Leu Glu Asn Arg Tyr Thr Ser Lys<br>1                  5                      10                 15 | 48 |
| AAA TAT GAC CCA TCA AAG AAA GTA TCT CAA GAA GAT TTA GCG GTT TTG<br>Lys Tyr Asp Pro Ser Lys Lys Val Ser Gln Glu Asp Leu Ala Val Leu<br>                 20                    25                   30 | 96 |
| CTT GAG GCT CTG CGT TTA TCT GCT TCT TCA ATT AAT TCA CAG CCT TGG<br>Leu Glu Ala Leu Arg Leu Ser Ala Ser Ser Ile Asn Ser Gln Pro Trp<br>        35                    40                  45 | 144 |
| AAA TTC ATT GTT ATT GAA TCC GAT GCA GCG AAG CAA GGT ATG CAT GAT<br>Lys Phe Ile Val Ile Glu Ser Asp Ala Ala Lys Gln Gly Met His Asp<br>        50                    55                  60 | 192 |
| TCG TTT GCA AAT ATG CAT CAG TTT AAT CAA CCT CAC ATC AAA GCG TGT<br>Ser Phe Ala Asn Met His Gln Phe Asn Gln Pro His Ile Lys Ala Cys<br>65                 70                    75                 80 | 240 |
| TCT CAT GTG ATT TTA TTT GCA AAT AAG CTT TCG TAT ACA CGA GAT GAT<br>Ser His Val Ile Leu Phe Ala Asn Lys Leu Ser Tyr Thr Arg Asp Asp<br>                 85                    90                   95 | 288 |
| TAT GAT GTG GTT TTA TCT AAA GCG GTT GCT GAC AAG CGT ATT ACT GAA<br>Tyr Asp Val Val Leu Ser Lys Ala Val Ala Asp Lys Arg Ile Thr Glu<br>                100                 105               110 | 336 |
| GAG CAA AAA GAA GCT GCT TTT GCT TCG TTT AAG TTT GTA GAA TTG AAC<br>Glu Gln Lys Glu Ala Ala Phe Ala Ser Phe Lys Phe Val Glu Leu Asn<br>              115                   120               125 | 384 |
| TGT GAT GAA AAT GGT GAG CAT AAA GCA TGG ACT AAG CCT CAA GCT TAT<br>Cys Asp Glu Asn Gly Glu His Lys Ala Trp Thr Lys Pro Gln Ala Tyr<br>130                 135                   140 | 432 |
| TTA GCT CTT GGT AAT GCT CTG CAT ACA TTA GCT AGA CTG AAC ATT GAC<br>Leu Ala Leu Gly Asn Ala Leu His Thr Leu Ala Arg Leu Asn Ile Asp<br>145                 150                   155               160 | 480 |
| TCA ACA ACA ATG GAA GGC ATT GAT CCT GAA TTA TTG AGT GAA ATT TTT<br>Ser Thr Thr Met Glu Gly Ile Asp Pro Glu Leu Leu Ser Glu Ile Phe<br>              160                   170               175 | 528 |
| GCT GAT GAA TTA AAA GGG TAT GAA TGT CAT GTT GCT TTA GCC ATT GGT<br>Ala Asp Glu Leu Lys Gly Tyr Glu Cys His Val Ala Leu Ala Ile Gly<br>              180                   185               190 | 576 |
| TAT CAT CAT CCA AGC GAA GAT TAT AAT GCC TCT TTG CCT AAG TCT CGT<br>Tyr His His Pro Ser Glu Asp Tyr Asn Ala Ser Leu Pro Lys Ser Arg<br>              195                   200               205 | 624 |
| AAG GCA TTT GAA GCA GTA ATT ACC ATC CTT TAG<br>Lys Ala Phe Glu Ala Val Ile Thr Ile Leu ***<br>210                         215 | 657 |

Fig. 3

```
TGTCACATAT GGCAAATTAA ATATTGAGTA TGCCTTGCTT GTTGACATCA TAAGTTGTGC    60
AGACAAGAAT GTCTGTGGAT TAAAATTTCA CAAGTAAGGT TTATTATT ATG ACG CAT   117
                                                     Met Thr His
                                                       1
CCA ATT ATT CAT GAT CTT GAA AAT CGT TAT ACA TCA AAA AAA TAT GAC   165
Pro Ile Ile His Asp Leu Glu Asn Arg Tyr Thr Ser Lys Lys Tyr Asp
      5                   10                  15
CCA TCA AAG AAA GTA TCT CAA GAA GAT TTA GCG GTT TTG CTT GAG GCT   213
Pro Ser Lys Lys Val Ser Gln Glu Asp Leu Ala Val Leu Leu Glu Ala
 20              25                  30                  35
CTG CGT TTA TCT GCT TCT TCA ATT AAT TCA CAG CCT TGG AAA TTC ATT   261
Leu Arg Leu Ser Ala Ser Ser Ile Asn Ser Gln Pro Trp Lys Phe Ile
                 40                  45                  50
GTT ATT GAA TCC GAT GCA GCG AAG CAA GGT ATG CAT GAT TCG TTT GCA   309
Val Ile Glu Ser Asp Ala Ala Lys Gln Gly Met His Asp Ser Phe Ala
                 55                  60                  65
AAT ATG CAT CAG TTT AAT CAA CCT CAC ATC AAA GCG TGT TCT CAT GTG   357
Asn Met His Gln Phe Asn Gln Pro His Ile Lys Ala Cys Ser His Val
         70                  75                  80
ATT TTA TTT GCA AAT AAG CTT TCG TAT ACA CGA GAT GAT TAT GAT GTG   405
Ile Leu Phe Ala Asn Lys Leu Ser Tyr Thr Arg Asp Asp Tyr Asp Val
         85                  90                  95
GTT TTA TCT AAA GCG GTT GCT GAC AAG CGT ATT ACT GAA GAG CAA AAA   453
Val Leu Ser Lys Ala Val Ala Asp Lys Arg Ile Thr Glu Glu Gln Lys
100                 105                 110                 115
GAA GCT GCT TTT GCT TCG TTT AAG TTT GTA GAA TTG AAC TGT GAT GAA   501
Glu Ala Ala Phe Ala Ser Phe Lys Phe Val Glu Leu Asn Cys Asp Glu
                120                 125                 130
AAT GGT GAG CAT AAA GCA TGG ACT AAG CCT CAA GCT TAT TTA GCT CTT   549
Asn Gly Glu His Lys Ala Trp Thr Lys Pro Gln Ala Tyr Leu Ala Leu
                135                 140                 145
GGT AAT GCT CTG CAT ACA TTA GCT AGA CTG AAC ATT GAC TCA ACA ACA   597
Gly Asn Ala Leu His Thr Leu Ala Arg Leu Asn Ile Asp Ser Thr Thr
            150                 155                 160
ATG GAA GGC ATT GAT CCT GAA TTA TTG AGT GAA ATT TTT GCT GAT GAA   645
Met Glu Gly Ile Asp Pro Glu Leu Leu Ser Glu Ile Phe Ala Asp Glu
            160                 170                 175
TTA AAA GGG TAT GAA TGT CAT GTT GCT TTA GCC ATT GGT TAT CAT CAT   693
Leu Lys Gly Tyr Glu Cys His Val Ala Leu Ala Ile Gly Tyr His His
180                 185                 190                 195
CCA AGC GAA GAT TAT AAT GCC TCT TTG CCT AAG TCT CGT AAG GCA TTT   741
Pro Ser Glu Asp Tyr Asn Ala Ser Leu Pro Lys Ser Arg Lys Ala Phe
                200                 205                 210
GAA GCA GTA ATT ACC ATC CTT                                       762
Glu Ala Val Ile Thr Ile Leu
                215
TAGATTCTTA ATGTTTGAGA TGAAGAAAAG CCAGCGATTT AGCTGTGCTT TGTTTGTGCA   822
***
AAAATGTTCC TAATGGCGTA TTACTACGGT AGGAAGTCTA TTTAAAGTTT CTTTTACTCT   882
TTGGTATTAA TTGTCAATTA CGCGGAAATC ATTATCTAAC TAGGCCT                929
```

Fig. 4

| | | | | | | | | | | | | | |
|---|---|---|---|---|---|---|---|---|---|---|---|---|---|
|Met|Thr|His|Pro|Ile|Ile|His|Asp|Leu|Glu|Asn|Arg|Tyr|Thr|Ser|Lys
1| | | |5| | | | |10| | | | |15

Met Thr His Pro Ile Ile His Asp Leu Glu Asn Arg Tyr Thr Ser Lys
 1           5             10              15
Lys Tyr Asp Pro Ser Lys Lys Val Ser Gln Glu Asp Leu Ala Val Leu
             20              25              30
Leu Glu Ala Leu Arg Leu Ser Ala Ser Ser Ile Asn Ser Gln Pro Trp
         35              40              45
Lys Phe Ile Val Ile Glu Ser Asp Ala Ala Lys Gln Gly Met His Asp
         50              55              60
Ser Phe Ala Asn Met His Gln Phe Asn Gln Pro His Ile Lys Ala Cys
 65              70              75              80
Ser His Val Ile Leu Phe Ala Asn Lys Leu Ser Tyr Thr Arg Asp Asp
                 85              90              95
Tyr Asp Val Val Leu Ser Lys Ala Val Ala Asp Lys Arg Ile Thr Glu
             100             105             110
Glu Gln Lys Glu Ala Ala Phe Ala Ser Phe Lys Phe Val Glu Leu Asn
         115             150             125
Cys Asp Glu Asn Gly Glu His Lys Ala Trp Thr Lys Pro Gln Ala Tyr
         130             135             140
Leu Ala Leu Gly Asn Ala Leu His Thr Leu Ala Arg Leu Asn Ile Asp
145             150             155             160
Ser Thr Thr Met Glu Gly Ile Asp Pro Glu Leu Leu Ser Glu Ile Phe
             165             170             175
Ala Asp Glu Leu Lys Gly Tyr Glu Cys His Val Ala Leu Ala Ile Gly
             180             185             190
Tyr His His Pro Ser Glu Asp Tyr Asn Ala Ser Leu Pro Lys Ser Arg
         195             200             205
Lys Ala Phe Glu Ala Val Ile Thr Ile Leu
210             215

```
                         5                    10
          Met-Thr-His-Pro-Ile-Ile-His-Asp-Leu-Glu-Asn-Arg-Tyr
FR1 : 5'ATG-ACT-CAT-CCT-AT 3'
           C   C   C
           A       A
           G       G
                    15                   20
          -Thr-Ser-Lys-Lys-Tyr-Asp-Pro-Ser-Lys-Lys-Val- ...

FR2 : 5'AAA-AAA-TAT-GAT-CC 3'
             G   G   C   C
```

GENE ENCODING ENZYME HAVING FLAVIN REDUCING ACTIVITY AND NITROREDUCTASE ACTIVITY

This application is a continuation of now abandoned application, Ser. No. 07/987,216, filed Dec. 8, 1992, now abandoned.

BACKGROUND OF THE INVENTION (i) Field of the Invention

The present invention relates to a gene encoding an enzyme having a flavin reducing activity and a nitroreductase activity, the enzyme produced therefrom, a recombinant vector containing the gene and bacteria containing the recombinant vector.

(ii) Description of the Related Art

A bacterial luciferase derived from luminous bacteria is used to produce oxidized flavin adenine mononucleotide (hereinafter referred to as "oxidized FMN") and a long-chain carboxylic acid in the presence of a long-chain aliphatic aldehyde, oxygen and a reduced flavin adenine mononucleotide (hereinafter referred to as "$FMNH_2$") as a luminescent substrate, and in this case, the bacterial luciferase catalyzes a reaction in which blue light is emitted. $FMNH_2$ which is a substrate can be obtained from a reduced nicotinamide adenine dinucleotide: flavin mononucleotide (NADH:FMN) reductase and a reduced nicotinamide adenine dinucleotide phosphate: flavin mononucleotide (NADPH:FMN) reductase, and the long-chain aldehyde can be obtained from a fatty acid reductase complex.

In recent years, Spyrou et al. have isolated a flavin reductase gene from *Escherichia coli* and elucidated its primary structure, which is disclosed in Spyrou G., Haggard-Ljungquist E., Krook M., Jornvall H., Nilsson E. and Reichard P., J. Bacteriol, 173, p. 3673–3679 (1991).

Around us, there are many substances (mutagens) which damage chromosomal DNA, and during our lives we are exposed to these substances. Nitroarenes are members of one group of environmental mutagens, and they are contained in the exhaust gas of automobiles, the smoke of incinerators, the atmosphere of cities, the bottoms of rivers, the air in rooms where stoves are lighted, and the burnt portions of grilled chickens. Of nitroarenes having mutability and carcinogenicity, 2-nitrofluorene is well known.

A nitroarene itself does not react directly with DNA to damage the same, but a metabolite of the nitroarene gives rise to a mutation in DNA to damage the DNA. For example, it can be presumed that nitrofluorene is reduced to an N-hydroxy form in the cell of a microorganism by a nitroreductase and then activated by an o-acetyl transferase, to thus finally produce nitrenium ions which attack the DNA. Therefore, it can be considered that the reaction of the nitroreductase with 2-nitrofluorene is a rate determining step in the mutagenesis of DNA by 2-nitrofluorene.

Watanabe et al. have isolated a nitroreductase gene from Salmonella, which is disclosed in Watanabe M., Ishidate M, Jr and Nohmi T., Mutation Research, p. 216 211–220 (1989). Furthermore, its primary structure has been elucidated in Watanabe M., Ishidate M, Jr and Nohmi T., Nucleic Acid Research, 18, p. 1059 (1990).

As understood from the foregoing, the FMN reductase is essential to utilize the luminescent reaction of bacterial luciferase to the utmost. Therefore, the isolation of the FMN reductase gene permits preparing the enzyme in large quantities, and thus, an important object is the isolation of the gene encoding this enzyme.

Furthermore, the nitroreductase gene is useful to improve the detection sensitivity of the above-mentioned mutagen or carcinogen.

However, with regard to the isolation of the FMN reductase gene of luminous bacteria and the nitroreductase gene as well as the expression of them in *Escherichia coli*, no report has been made so far.

SUMMARY OF THE INVENTION

In view of the above-mentioned technical situation, an object of the present invention is to provide a gene encoding an enzyme having an FMN reducing activity of luminous bacteria and a nitroreductase activity and the enzyme therefor. Another object of the present invention is to provide a recombinant vector containing this gene and bacteria containing the recombinant vector.

As a result of intensive research, the present inventors have succeeded in isolating a gene encoding an enzyme having the FMN reducing activity and the nitroreductase activity from the luminous bacteria *Vibrio fischeri* (ATCC 7744), and in elucidating its primary structure. In addition, they have succeeded in cultivating *Escherichia coli* transformed with a vector containing the gene which can express the protein in large quantities. As a result, the present invention has now been completed.

The present invention has the following parts (1) to (8).

(1) A gene containing a nucleotide sequence shown in FIG. 1 (SEQ ID No. 1) and encoding an enzyme having a flavin reducing activity and a nitroreductase activity.

(2) A gene containing a nucleotide sequence shown in FIG. 2 (SEQ ID No. 2) and encoding an enzyme having the flavin reducing activity and the nitroreductase activity described in the previous paragraph (1).

(3) A gene containing a nucleotide sequence shown in FIG. 3 (SEQ ID No. 3) and encoding an enzyme having a flavin reducing activity and a nitroreductase activity.

(4) An enzyme containing an amino acid sequence shown in FIG. 4 (SEQ ID No. 4) and having a flavin reducing activity and a nitroreductase activity.

(5) A recombinant vector containing a DNA whose nucleotide sequence is shown in FIG. 1.

(6) The recombinant vector described in the previous paragraph (5) in which the gene having the nucleotide sequence shown in FIG. 1 is inserted into a plasmid vector.

(7) Bacteria containing a recombinant vector containing a DNA whose nucleotide sequence is shown in FIG. 1.

(8) A method for preparing an enzyme containing an amino acid sequence shown in FIG. 4 which comprises the step of cultivating bacteria transformed with a recombinant vector containing a DNA whose nucleotide sequence is shown in FIG. 1.

BRIEF DESCRIPTION OF THE DRAWINGS

FIG. 1 shows a nucleotide sequence of a gene encoding an enzyme having a flavin reducing activity and a nitroreductase activity.

Sequence length: 657

Sequence type: Nucleic acid

Strandedness: 1

Topology: Linear

Molecular type: Genomic DNA

Feature of sequence description:
  Feature key defined in Gene Bank Authorin Reference Manual Release 1.1 (hereinafter referred to simply as "feature key"): CDS Procedure for determining the feature:
  Prediction from an amino acid sequence of FIG. 4 based on genetic code table.

(On the left and right sides of each triplet, a 5' terminal and a 3' terminal are present, respectively. This triplet represents a purine base (Pu) and a pyrimidine base (Py) constituting a nucleotide sequence.

A: adenine,
  G: guanine,
  C: cytosine,
  R: A or G,
  Y: T or C,
  N: A, T, C or G,
  H: A, C or T,
  T: thymine, Base codon NTN: When the first base (N) of codon NTN is C, the third base (N) of codon is A, G, C or T; when the first base is T, the third base is A or G; when the third base is A or G, the first base is T or C; and when the third base is C or T, the first base is C.

Base codon NGN: When the first base (N) of codon NGN is C, the third base (N) is A, G, C or T; when the first base is A, the third base is A or G; when the third base is A or G, the first base is C or A; and when the third base is C or T, the first base is C. *** represents TAA, TAG or TGA.).

Under each triplet codon of the nucleotide sequence, the amino acid encoded thereby is represented.

FIG. 2 shows a typical nucleotide sequence of the gene encoding the enzyme having a flavin reducing activity and a nitroreductase activity.

Sequence length:657
  Sequence type: Nucleic acid
  Strandedness:1
  Topology: Linear
  Molecular type: Genomic DNA
  Original source:
  Organism: *Vibrio fischeri*
  Strain: ATCC 7744

Feature of sequence description:
  Feature key defined in Gene Bank Authorin Reference Manual Release 1.1: CDS Procedure for determining the feature:
  Experimental procedure.

FIG. 3 shows a nucleotide sequence of a gene encoding an enzyme having a flavin reducing activity and a nitroreductase activity.

Sequence length:929
  Sequence type: Nucleic acid
  Strandedness:1
  Topology: Linear
  Molecular type: Genomic DNA
  Original source:
    Organism: *Vibrio fischeri*
    Strain: ATCC 7744

Feature of sequence description:
  Feature key: CDS

Site having the feature:109–762
  Procedure for determining the feature:
    Experimental procedure.

FIG. 4 shows an amino acid sequence of an enzyme having a flavin reducing activity and a nitroreductase activity.

Sequence length:218
  Sequence type: Amino acid
  Molecular type: Protein.

Figures 5, 6:
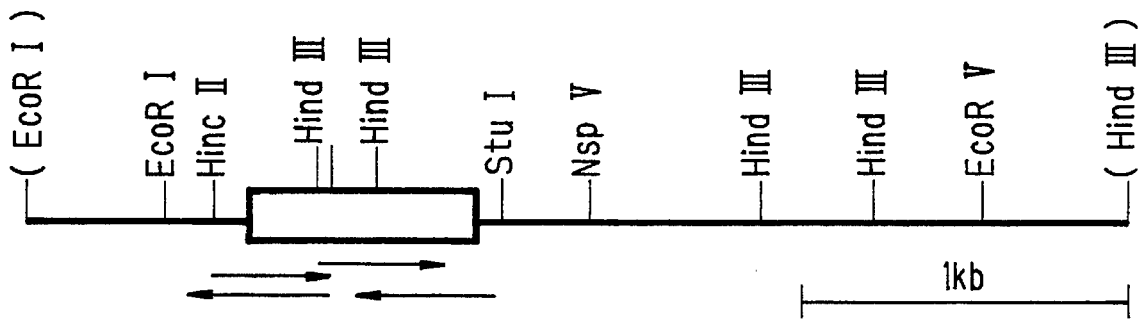

FIG. 5 shows an N-terminal amino acid sequence of an NAD(P)H: FMN reductase and synthetic oligonucleotide probes (FR1 and FR2) (SEQ ID NO.5).

FIG. 6 shows a restriction map of the gene of the present invention and a sequencing strategy. Arrows denote directions for the determination of the nucleotide sequences. The portion indicated by a box corresponds to the gene.

Figure 7:
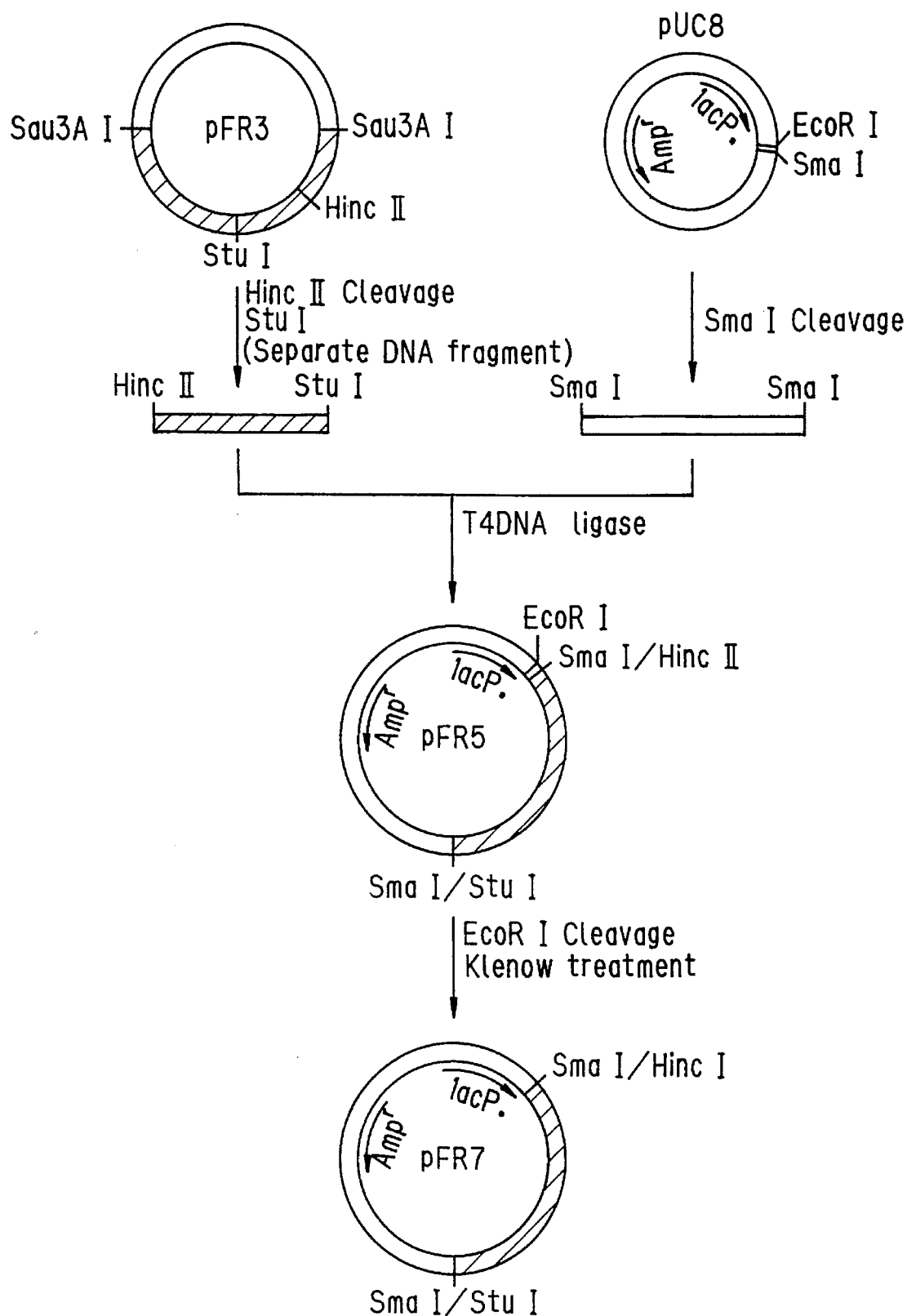

FIG. 7 shows a process of constructing a recombinant vector (an expression vector pFR7) containing a gene encoding an enzyme having an FNM reducing activity and a nitroreductase activity of luminous bacteria according to the present invention.

Figure 8:
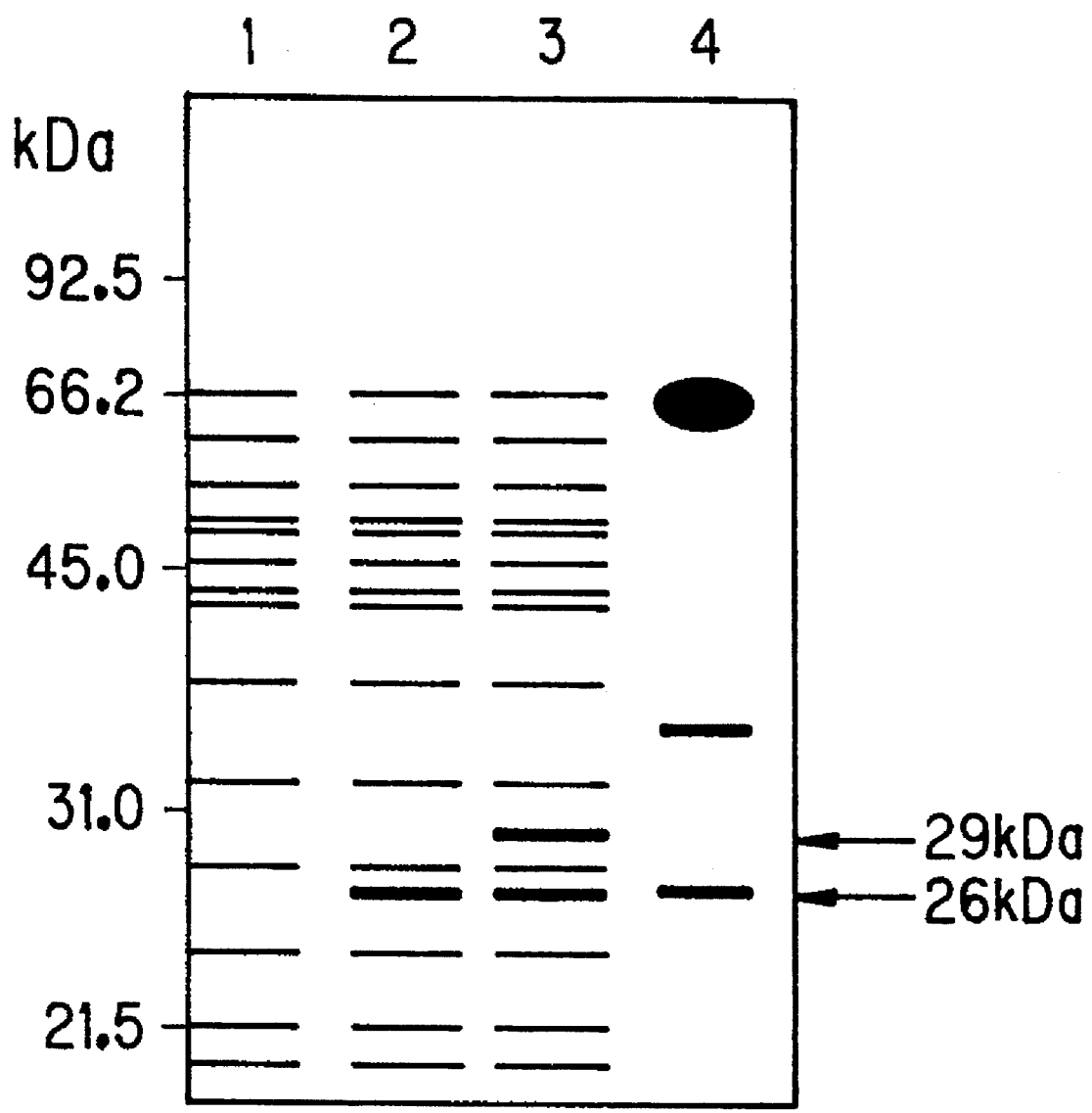

FIG. 8 shows the confirmation of the expressed protein by SDS-polyacrylamide gel electrophoresis. Lane 1 is a pUC8/D1210 strain, lane 2 is a pFR7/D1210 strain, lane 3 is a pFRS/D1210 strain, and lane 4 is a Boehringer Mannheim NAD(P)H: FMN reductase.

The symbols used in the drawings have the following meanings.

lacP . . . lactose promoter $Amp^r$ . . . Ampicillin resistant gene pUC8 . . . plasmid vector pFR3 . . . recombinant vector pFR5 . . . recombinant vector pFR7 . . . recombinant vector (expression vector)

Sau3AI . . . four bases (GATC) recognizing restriction enzyme

HincII . . . six bases (GTPyPuAC) recognizing restriction enzyme

SmaI . . . six bases (CCCGGG) recognizing restriction enzyme

StuI . . . six bases (AGGCCT) recognizing restriction enzyme

EcoRI . . . six bases (GAATTC) recognizing restriction enzyme

HindIII . . . six bases (AAGCTT) recognizing restriction enzyme

AccI . . . six bases ($GT_{CG}^{AT}AC$) recognizing restriction enzyme

NspV . . . six bases (TTCGAA) recognizing restriction enzyme

EcoRV . . . six bases (GATATC) recognizing restriction enzyme.

DETAILED DESCRIPTION OF PREFERRED EMBODIMENTS

The gene of the present invention is characterized by containing a nucleotide sequence having a sequence length of 657 bases as shown in FIG. 1. The nucleotide sequence in FIG. 1 can be predicted from an amino acid sequence shown in FIG. 4 as mentioned later.

A preferable sequence contains a nucleotide sequence as shown in FIG. 2.

A typical nucleotide sequence is a DNA having a sequence length of 929 bases as shown in FIG. 3.

The basic nucleotide sequence of the present invention is derived from Genomic DNA isolated from luminous bacteria *Vibrio fischeri* (ATCC 7744). This sequence is characterized by encoding a protein having a molecular weight of 24562 and comprising 218 amino acids, corresponding to nucleotides numbered 109 to 762.

The gene of the present invention encodes a protein having a flavin reducing activity and a nitroreductase activity, for example, an FMN reducing activity and a nitrofurazone reducing activity.

An enzyme of the present invention is a protein having an amino acid sequence shown in FIG. 4 which can be predicted from the nucleotide sequence in FIG. 3. This protein comprises 218 amino acids and has a molecular weight of 24562 and the two activities of luminous bacteria, i.e., the flavin reducing activity and the nitroreductase activity.

A recombinant vector of the present invention contains a DNA whose nucleotide sequence is shown in FIG. 1. That is, the recombinant vector of the present invention contains a nucleotide sequence which is the same or is functionally equal to the DNA having the nucleotide sequence shown in FIG. 3. A "functionally equal nucleotide sequence" means any DNA fragment which can be used in accordance with a substantially similar method to the present invention so as to obtain the substantially identical results, i.e. the production of an enzyme having the FMN reducing activity and the nitroreductase activity of luminous bacteria in a suitable host.

That is, the "functionally equal nucleotide sequence" means any DNA fragment which can encode a protein having the same amino acid sequence, even if the nucleotide sequence is different, or a DNA fragment which can code a protein having the FMN reducing activity and the nitroreductase activity, even if there is a slight difference in the amino acid sequence attributed to a slight difference in the nucleotide sequence. Typical examples are the nucleotide sequence of FIG. 3 and the nucleotide sequence of FIG. 1 into which a site-specific mutation may be introduced.

The nucleotide sequence in FIG. 1 will be described as follows:

Recently developed techniques make it possible to genetically endow a suitable microorganism with the ability to synthesize a protein or peptide normally made by another organism. The technique makes use of a fundamental relationship which exists in all living organisms between the genetic material, usually DNA, and the proteins synthesized by the organism. This relationship is such that the amino acid sequence of the protein is reflected in the nucleotide sequence of the DNA. There are one or more trinucleotide sequence groups specifically related to each of the twenty amino acids most commonly occurring in proteins. The specific relationship between each given trinucleotide sequence and its corresponding amino acid constitutes the genetic code. The genetic code is believed to be the same or similar for all living organisms. As a consequence, the amino acid sequence of every protein or peptide is reflected by a corresponding nucleotide sequence, according to a well understood relationship. Furthermore, this sequence of nucleotides can, in principle, be translated by any living organism.

The trinucleotides, termed codons, are presented as DNA trinucleotides, as they exist in the genetic material of a living organism. Expression of these codons in protein synthesis requires intermediate formation of messenger RNA (mRNA). The mRNA codons have the same sequences as the DNA codons, except that uracil is found in place of thymine. Complementary trinucleotide DNA sequences having opposite strand polarity are functionally equivalent to the codons, as is understood in the art. An important and well known feature of the genetic code is its redundancy, whereby, for most of the amino acids used to make proteins, more than one coding nucleotide triplet may be employed. Therefore, a number of different nucleotide sequences may code for a given amino acid sequence. Such nucleotide sequences are considered functionally equivalent since they can result in the production of the same amino acid sequence in all organisms, although certain strains may translate some sequences more efficiently than they do others. Occasionally, a methylated variant of a purine or pyrimidine may be found in a given nucleotide sequence. Such methylations do not affect the coding relationship in any way.

The typical example is a plasmid vector into which the DNA fragment having the nucleotide sequence is introduced. As this kind of vector, there can be used pUC [C. Yanisch-Perron, J. Vieira and J. Messing, Gene, 33, p. 110–115 (1985)] and pIN III [Y. Masui, J. Coleman, M. Inouye, Experimental Manipulation of Gene Expression (ed. M. Inouye ), Academic Press, p. 15 (1983)].

FIG. 7 shows a construction process of this recombinant vector (the expression vector).

That is, a vector pFR3 having a reductase gene is cleaved with restriction enzymes HincII and StuI to obtain a fragment including a coding region, and this fragment is then inserted into an SmaI site of a pUC8 plasmid DNA [Hanna Z., Fregeau C., Prefontaine G. and Brousseau R., Gene, p. 30247 (1984)] to construct a recombinant vector pFR5. Furthermore, this vector pFR5 is cleaved with a restriction enzyme EcoRI and then subjected to a Klenow treatment in the presence of dNTP. Afterward, the vector is recirculized using a T4 DNA ligase to construct a recombinant vector pFR7 (an expression vector). For the orientation of the thus constructed product, a restriction enzyme cleavage site is shown in an ampicillin resistant gene (Amp$^r$).

Bacteria of the present invention contain a recombinant vector DNA having the nucleotide sequence shown in FIG. 1. The bacteria of the present invention are characterized by producing a protein having the flavin reducing activity and the nitroreductase activity.

A method for preparing the enzyme of the present invention comprises the steps of cultivating bacteria modified with a recombinant vector (an expression vector) containing a DNA whose nucleotide sequence is shown in FIG. 3, and then producing a protein containing an amino acid sequence shown in FIG. 4. Examples of the bacteria include *Escherichia coli* and *Bacillus subtilis*, and examples of a culture medium to be used include an LB culture medium and a YT culture medium.

A gene of the present invention is that which has been isolated for the first time encoding an enzyme having an FMN reducing activity and a nitroreductase activity. This gene can be used to produce a highly sensitive strain of bacteria to a mutagen or a carcinogen by the use of a suitable host such as *Escherichia coli*. Additionally, from this *Escherichia coli*, a reductase protein can also be prepared in large quantities.

By inserting this expression vector into a suitable host such as *Escherichia coli*, organisms or bacteria can be produced which express an enzyme having the FMN reducing activity and the nitroreductase activity of luminous bacteria. Furthermore, the reductase can also be prepared in large quantities by extraction from the organisms into which the gene is introduced. The organisms or microorganisms into which the gene is introduced have a high sensitivity to a mutagen or a carcinogen owing to the above-mentioned function, and thus they are useful as an indicator for detecting the mutagen or the carcinogen.

The reductase amplifies a luminous reaction of bacterial luciferase owing to the above-mentioned function. Thus, the reductase can be applied to many measuring methods and it is useful, for example, as a diagnosis drug or an inspection drug.

EXAMPLES

Now, the isolation and identification of a gene which is important to the present invention will be described in reference to examples.

Example 1

[Identification of NAD(P)H: FMN reductase and determination of N-terminal amino acid sequence]

An NAD(P)H: FMN reductase sample (available from Boehringer Mannheim) was introduced into a "Sparose 12" gel filtration column (made by Pharmacya Co., Ltd. ) to fractionate the sample. For each fraction, NADH and NADPH: FMN reducing activities were measured by a procedure described in Jablonski E. and DeLuca M., Biochemistry, 16, p. 2932 (1977), and analysis was then made in accordance with a procedure described in Laemmli, U.K. Nature, 277, p. 680 (1970) by means of sodium dodecyl sulfate-polyacrylamide gel electrophoresis.

AS a result, it was clarified that the FMN reducing activity is directly proportional to the amount of a protein of 26 kDa (which is denoted by an arrow in After an SDS-PAGE analysis of this protein, it was transferred into a nylon membrane, and its amino acid sequence was determined in a usual manner by the use of a protein sequencer [made by Applied Biosystems Inc. (ABI)]. The results are set forth in FIG. 5. From these results, an N-terminal amino acid sequence having sequence numbers of 1 to 24 was confirmed.

Example 2

[Preparation of luminescent bacteria genomic library]

A photobacterium medium containing luminescent bacteria *Vibrio fischeri* (ATCC7744) was shaken at 26° C. overnight to cultivate the bacteria. The bacteria were collected by means of centrifugal separation at 10000 rpm, and the resultant cell pellets were then dispersed in a Tris-HCl.EDTA buffer solution (hereinafter referred to as "a TE buffer"). After a lysozyme treatment at 37° C. for 1 hour, sodium dodecyl sulfate (hereinafter abbreviated to "SDS") was added, followed by a proteinase K treatment at 50° C. for 3 hours. Afterward, a phenol treatment was carried out three times, followed by ethanol precipitation. After drying, the dried material was dissolved in the TE buffer, and then subjected to the proteinase K treatment again. Afterward, the three cycles of the phenol treatment and then the ethanol precipitation were carried out to recover the genomic DNA. 10 units of a restriction enzyme Sau3AI were reacted with 50 μm of this genomic DNA at 37° C. Some parts of the reaction mixture were taken out at reaction times of 5, 10, 20, 30, 45, 60, 90 and 120 minutes, and afterward, EDTA (ethylenediaminetetraacetic acid ) was added to the reaction system to bring the reaction to an end. Each part of the DNA was subjected to agarose gel electrophoresis to confirm the degree of partial decomposition of the genomic DNA. The reaction solutions at the respective times were combined into one, followed by the ethanol precipitation, to recover the DNA. Next, this DNA was dissolved in a small amount of the TE buffer, and then subjected to agarose gel electrophoresis to recover a fraction of 4 to 6 Kb by the use of a DE81 paper. The DNA fraction of 4 to 6 Kb was dissolved out of the DE81 paper with 1M NaCl, subjected to the phenol treatment three times, and then precipitated with ethanol. The sample was dissolved in the TE buffer so as to be about 200 ng/μl. Afterward, the DNA fraction of 4 to 6 Kb was reacted with a pUC18 plasmid DNA (a plasmid vector), which was previously cleaved with a restriction enzyme BamH I and then treated with an alkaline phosphatase (an enzyme for catalyzing dephosphorization at the 5' terminal of the DNA), at 16° C. overnight in the presence of a T4 DNA ligase (an enzyme for ligating DNA chains to each other or ligating the DNA and the 3'OH of an RNA or the 5'P terminal by a phosphodiester bond), whereby the DNA fraction was ligated to the plasmid. The resultant ligation reaction solution was transferred to JM109 *Escherichia coli* so as to perform transformation, and the thus obtained transductant represented a gene library.

[Preparation of synthetic oligonucleotide probe]

On the basis of the information of an amino acid sequence shown in FIG. 5, two probes of an oligonucleotide probe (FR-1) and an oligonucleotide probe (FR-2) were synthesized by means of a DNA synthesizer (made by ABI). Each synthetic probe was purified by the use of an OPC cartridge (made by ABI).

[Cloning of NAD(P)H: FMN reductase gene and analysis of its structure]

The gene library of Example 2 was screened in accordance with a colony hybridization method by the use of the FR-1 probe and the FR-2 probe. The FR-1 probe and the FR-2 probe were labelled at the 5' terminal with [γ-$^{32}$P]ATP and then used as labelled probes. After the titer of the gene library was measured, this gene library was scattered on a nitrocellulose filter so as to be 200 colonies per plate. Cultivation was made at 37° C. overnight, and two replicas were taken per filter. Each pair of two replicas was cultivated at 37° C. and then used for hybridization. The filter was air-dried and then irradiated with ultraviolet rays (UV) to fix the DNA. Afterward, the filter was put in a hybridization solution {20 ml of a 6×SET buffer [20×SET buffer:3M of NaCl, 0.6M of Tris-HCl (pH 8.0) and 0.04M of EDTA], a 10×Dehhardt's solution [(a solution containing 0.2% of each of serum albumin, polyvinylpyrrolidone and Ficoll), a 0.1% SDS and a salmon sperm DNA (thermally denatured, 50 μm/ml)], and it was then maintained at 68° C. for 1 hour. Furthermore, the solution was replaced with a new one and then maintained for 1 hour, and a $^{32}$P-levelling probe was added, followed by hybridization at room temperature overnight. The solution was thrown away, and the filter was then washed with the 6×SET buffer, followed by shaking at 37° C. for 20 minutes. After this operation was repeated twice, the filter was air-dried and then subjected to autoradiography. The filter was superposed upon a developed X-ray film, and the position of an ink marker was photographed on the film. Identification was made by aligning signals which were coincident with each other on the two films of the probe FR-1 and the probe FR-2 made from the one plate, and thus, five identified colonies (clones ) were obtained.

[Preparation of recombinant vector]

For these five clones, a restriction analysis was carried out (FIG. 6), and as a result, it was apparent that three of these five clones were the same clones, which meant that three kinds of positive clones were prepared. Above all, a recombinant vector pFR3 (FIG. 7) having the smallest inserted DNA was used for the subsequent analysis.

[Structure determination of the gene and determination of amino acid sequence]

A Southern blotting analysis was made by the use of the FR-1 probe, and the region of an FMN reductase gene was determined in accordance with a dideoxynucleotide-enzyme method [Hattori M. and Sakaki Y., Anal, Biochem., 152, p. 232 (1986)], whereby a primary structure shown in FIG. 3 was elucidated. As a result, it was understood that the FMN reductase gene encoded a polypeptide of 24562 Da comprising 218 amino acids shown in FIG. 4, and this gene was about 30% homologous with a nitroreductase gene of Salmonella [Watanabe M., Ishidate M. Jr and Nohmi T., Nucleic Acid Res., 18, p. 1059 (1990)].

Example 3

[Recombinant vector of NAD(P)H: FMN reductase gene, and construction of expression vector] (FIG. 7)

A recombinant vector pFR3 plasmid DNA was cleaved with a restriction enzyme Hinc II/Stu I and then treated at −80° C. for 10 minutes. The thus treated DNA was then subjected to agarose gel electrophoresis to separate and recover a DNA fragment of about 1 Kb by the use of a DE81 paper. The DNA was dissolved out of the DE81 paper with 1M NaCl subjected to the phenol treatment three times, and then precipitated with ethanol. Next, the sample was dissolved in the TE buffer so as to be about 200 The above-mentioned DNA was reacted, at 16° C. overnight in the presence of a T4DNA ligase, with a pUC8 plasmid DNA (a plasmid vector) which was previously cleaved with a restriction enzyme Sma I and then treated with an alkaline phosphatase, whereby the DNA was ligated to the plasmid. The resultant ligation reaction solution was transferred to JM109 *Escherichia coli* to perform transformation, and the *Escherichia coli* was selected and then cultivated overnight in a culture medium containing 5-bromo-4-chloro-3-indolyl-β-D-galactoside (Xgal) to form a white colony. This white colony was a transductant containing the plasmid into which the heterologous DNA was inserted.

A plasmid DNA was prepared from these transductants, and a restriction analysis was then carried out to obtain a strain containing a transformed vector pFR5. A plasmid DNA of the recombinant vector pFR5 was prepared, cleaved with EcoR I, subjected to a Klenow treatment, ligated with a T4DNA ligase, and then was transferred to D1210 *Escherichia coli* to perform transformation. Of the transductants, one in which an EcoR I cleavage site disappeared was selected. This was a recombinant vector (an expression vector) pFR7.

The recombinant vector pFR5 was constructed so as to express a peptide derived from a N-terminal β-galactosidase gene (lacZ) and a fused protein of the FMN reductase enzyme. The expression vector pFR7 was constructed so as to express lacZ and frameshift FMN reductase singly.

Example 4

[Preparation of *Escherichia coli* incorporated with NAD(P)H: FMN reductase gene]

Expression vectors pFR5 and pFR7 and a pUC8 plasmid DNA were transferred to D1210 *Escherichia coli* to perform transformation.

[Preparation of enzyme]

These transductants were incubated overnight, and 0.25 ml of the resultant incubation solution was transferred to an LB liquid (10 ml) culture medium containing ampicillin. After the culture medium was shaken at 37° C. for 2 hours to cultivate the transductants, isopropyl-β-D(−)-thiolactopyranoside (hereinafter abbreviated to "IPTG") was added thereto so that a final concentration might be 1 mM, and the transductants were further cultivated for 3 hours. For the bacteria, an SDS-PAGE analysis was carried out to confirm the expression of a protein (this protein corresponds to the enzyme of the present invention).

The results are set forth in FIG. 4, but in the cases of the recombinant vectors pFR5 and pFR7, new bands appeared at 26 kDa which was the same size as in a commercial crude enzyme sample. In addition, in the case of the recombinant vector pFR5, a band appeared even at 29 kDa, and this vector was considered to be derived from a fused protein with lac Z.

1.5 ml of the incubation solution which was subjected to an IPTG induction treatment was centrifugally separated at 10000 rpm to remove a supernatant. The bacteria were dispersed in 0.5 ml of a 50 mM potassium phosphate.1 mM dithiothreitol buffer, and then sonically disrupted by ultrasound. Centrifugal separation was further carried out at 4° C. for 30 minutes at 12000 rpm, and the resultant supernatant was a cell extract.

For this cell extract, the following enzyme reducing activity was measured. The results are set forth in Tables 1, 2 and 3.

(1) Flavin reducing activity: This was measured in accordance with a procedure described in Jablonski E and Deluca M., Biochemistry, 16, p. 2932 (1977).

(2) Iron reducing activity: This was measured in accordance with a procedure described in Fontecave M., Eliasson R. and Reichard P., J. Biol. Chem., 262., p. 12325–12331 (1987).

(3) Nitroreductase activity: This was measured in accordance with a procedure described in Watanabe M., Ishidate M. Jr. and Nohmi T., Mutation Research, 216, p. 211–220 (1989).

Protein amounts in the respective tables were determined in accordance with a Bradford method by the use of a protein assay kit made by Bio-RAD [Bradford M. M., Anal. Biochem., 72, p. 248–254 (1976)].

TABLE 1

| | | Flavin Reducing Activity mol/min/mg protein) | | | | | |
|---|---|---|---|---|---|---|---|
| | Strain | FMN | | FAD | | Riboflavin | |
| | (IPTG) | (+) | (−) | (+) | (−) | (+) | (−) |
| NADH | pFR5/D1210 | 6330 | 430 | 3980 | 240 | 2120 | 80 |
| | pFR7/D1210 | 11810 | 660 | 7410 | 340 | 2700 | 50 |
| | pUC13/D1210 | 20 | 30 | 50 | 40 | 10 | 0 |
| | D1210 | 40 | 30 | 40 | 10 | 10 | 0 |
| NADPH | pFR5/D1210 | 2300 | 190 | 1680 | 70 | 660 | 10 |
| | pFR7/D1210 | 4430 | 230 | 2840 | 140 | 870 | 110 |
| | pUC13/D1210 | 50 | 30 | 0 | 10 | 0 | 50 |
| | D1210 | 20 | 50 | 10 | 30 | 10 | 0 |

TABLE 2

| | Strain | Iron Reductase Activity (nmol/min/mg protein) | | | | | |
|---|---|---|---|---|---|---|---|
| | | FMN | | FAD | | Riboflavin | |
| | (IPTG) | (+) | (−) | (+) | (−) | (+) | (−) |
| NADH | pFR5/D1210 | 44.9 | 4.5 | 39.4 | 3.6 | 30.1 | 2.9 |
| | pFR7/D1210 | 68.3 | 6.6 | 59.5 | 5.4 | 42.8 | 4.2 |
| | pUC13/D1210 | 0.4 | 0.1 | 1.6 | 1.7 | 0.1 | 0.0 |
| | D1210 | 0.4 | 0.2 | 1.3 | 1.8 | 0.0 | 0.0 |
| NADPH | pFR5/D1210 | 12.6 | 1.5 | 11.8 | 0.4 | 9.4 | 0.3 |
| | pFR7/D1210 | 25.8 | 2.5 | 23.6 | 1.3 | 14.0 | 0.5 |
| | pUC13/D1210 | 0.6 | 0.4 | 0.1 | 0.0 | 0.2 | 0.0 |
| | D1210 | 0.6 | 0.3 | 0.1 | 0.0 | 0.4 | 0.0 |

TABLE 3

| | Strain | Nitroreductase Activity (nmol/min/mg protein) Nitrofurazone | |
|---|---|---|---|
| | (IPTG) | (+) | (−) |
| NADPH | pFR5/D1210 | 24.8 | 10.1 |
| | pFR7/D1210 | 40.9 | 10.4 |
| | pUC13/D1210 | 4.7 | 5.2 |
| | D1210 | 6.8 | 5.5 |

Comparing the activities in these tables, the activities of pFR5 and pFR7 are about 1 to 3 orders higher than those of pUC13 which is a negative control. This gene could therefore be identified as a gene encoding an enzyme protein having a flavin reducing activity and a nitroreductase activity.

What is claimed is:

1. An isolated and purified gene containing a nucleotide sequence shown in SEQ ID NO: 1 and encoding an enzyme having a flavin reducing activity and a nitroreductase activity.

2. An isolated and purified gene containing a nucleotide sequence shown in SEQ ID NO: 2 and encoding an enzyme having a flavin reducing activity and a nitroreductase activity.

3. An isolated and purified gene containing a nucleotide sequence shown in SEQ ID NO: 3 and encoding an enzyme having a flavin reducing activity and a nitroreductase activity.

4. A recombinant vector containing a DNA whose nucleotide sequence is shown in SEQ ID NO: 1.

5. The recombinant vector according to claim 4 wherein the nucleotide sequence shown in SEQ ID NO: 1 is inserted into a plasmid vector.

6. A bacterial host containing a recombinant vector which vector contains a DNA whose nucleotide sequence is shown in SEQ ID NO: 1.

7. A method for preparing an enzyme containing an amino acid sequence shown in SEQ ID NO: 4 which comprises a step of cultivating bacteria modified with a recombinant vector containing a DNA whose nucleotide sequence is shown in SEQ ID NO: 1.

\* \* \* \* \*

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
      ( A ) LENGTH: 657 bases
      ( B ) TYPE: nucleic acid
      ( C ) STRANDEDNESS: single
      ( D ) TOPOLOGY: linear ( i i ) MOLECULE TYPE: genomic DNA ( i i i ) HYPOTHETICAL:

( i v ) ANTI-SENSE:

( v ) FRAGMENT TYPE:

( v i ) ORIGINAL SOURCE:
      ( A ) ORGANISM:
      ( B ) STRAIN:
      ( C ) INDIVIDUAL ISOLATE:
      ( D ) DEVELOPMENTAL STAGE:
      ( E ) HAPLOTYPE:
      ( F ) TISSUE TYPE:
      ( G ) CELL TYPE:
      ( H ) CELL LINE:
      ( I ) ORGANELLE:

( v i i ) IMMEDIATE SOURCE:
      ( A ) LIBRARY:
      ( B ) CLONE:

( v i i i ) POSITION IN GENOME:
      ( A ) CHROMOSOME/SEGMENT:
      ( B ) MAP POSITION:
      ( C ) UNITS:

( i x ) FEATURE:
      ( A ) NAME/KEY: Base
      ( B ) LOCATION: All
      ( C ) IDENTIFICATION METHOD:
      ( D ) OTHER INFORMATION: /note ="R is A or G"

( i x ) FEATURE:
      ( A ) NAME/KEY: Base
      ( B ) LOCATION: All
      ( C ) IDENTIFICATION METHOD:
      ( D ) OTHER INFORMATION: /note ="Y is T or C"

( i x ) FEATURE:

(A) NAME/KEY: Base
(B) LOCATION: 6, 12, 42, 45, 60, 63, 72, 75, 90, 93, 105,
117, 120, 123, 126, 135, 141, 156, 165, 174, 183, 195,
201, 225, 237, 243, 261, 273, 279, 300, 306, 312, 315,
318, 333, 351, 354, 360, 363, 375, 399, 411, 417, 423,
429, 438, 444, 450, 459, 465, 483, 486, 489, 498, 507,
519.
(C) IDENTIFICATION METHOD:
(D) OTHER INFORMATION: /note ="N is A, T, C or G"

(ix) FEATURE:
(A) NAME/KEY: Base
(B) LOCATION: 546, 561, 564, 570, 576, 588, 591, 606, 609,
615, 621, 630, 639, 642, 648.
(C) IDENTIFICATION METHOD:
(D) OTHER INFORMATION: /note ="N is A, T, C or G"

(ix) FEATURE:
(A) NAME/KEY: Base
(B) LOCATION: All
(C) IDENTIFICATION METHOD:
(D) OTHER INFORMATION: /note ="H is A, C or T"

(ix) FEATURE:
(A) NAME/KEY: Base codon NTN
(B) LOCATION: 25-27, 85-87, 94-96, 97-99, 106-108, 112-114,
253-255, 268- 270, 301-303, 433-435, 439-441, 451-453,
460-462, 469- 471, 511-513, 538-540, 565-567,
and 652- 654.
(C) IDENTIFICATION METHOD:
(D) OTHER INFORMATION: /note ="When the first base (N) of
codon NTN is C, the third base (N) of codon is A, G, C
or T; when the first base is T, the third base is A or
G; when the third base is A or G, the first base is T
or C; and when third base is C or T, the first base
is C"

(ix) FEATURE:
(A) NAME/KEY: Base codon NGN
(B) LOCATION: 34-36, 109-111, 280- 282, 325-327, 466-468,
and 622- 624.
(C) IDENTIFICATION METHOD:
(D) OTHER INFORMATION: /note ="When the first base (N) of
codon NGN is C, the third base (N) is A, G, C or T;
when the first base is A, the third base is A or G;
when the third base is A or G, the first base is C or
A; and when the third base is C or T, the first base
is C"

(x) PUBLICATION INFORMATION:
(A) AUTHORS:
(B) TITLE:
(C) JOURNAL:
(D) VOLUME:
(E) ISSUE:
(F) PAGES:
(G) DATE:
(H) DOCUMENT NUMBER:
(I) FILING DATE:
(J) PUBLICATION DATE:
(K) RELEVANT RESIDUES IN SEQ ID NO:

(xi) SEQUENCE DESCRIPTION: SEQ ID NO:1:

```
ATG  ACN  CAY  CCN  ATH  ATH  CAY  GAY  NTN  GAR  AAY  NGN  TAY  ACN  TCN  AAR      48
Met  Thr  His  Pro  Ile  Ile  His  Asp  Leu  Glu  Asn  Arg  Tyr  Thr  Ser  Lys
 1                   5                        10                       15

AAR  TAY  GAY  CCN  TCN  AAR  AAR  GTN  TCN  CAR  GAR  GAY  NTN  GCN  GTN  NTN      96
Lys  Tyr  Asp  Pro  Ser  Lys  Lys  Val  Ser  Gln  Glu  Asp  Leu  Ala  Val  Leu
              20                        25                       30

NTN  GAR  GCN  NTN  NGN  NTN  TCN  GCN  TCN  TCN  ATH  AAY  TCN  CAR  CCN  TGG     144
Leu  Glu  Ala  Leu  Arg  Leu  Ser  Ala  Ser  Ser  Ile  Asn  Ser  Gln  Pro  Trp
         35                        40                       45

AAR  TTY  ATH  GTN  ATH  GAR  TCN  GAY  GCA  GCN  AAR  CAR  GGN  ATG  CAY  GAY     192
Lys  Phe  Ile  Val  Ile  Glu  Ser  Asp  Ala  Ala  Lys  Gln  Gly  Met  His  Asp
     50                        55                       60
```

| | | | | | | | | | | | | | | | | |
|---|---|---|---|---|---|---|---|---|---|---|---|---|---|---|---|---|
| TCN | TTY | GCN | AAY | ATG | CAY | CAR | TTY | AAY | CAR | CCN | CAY | ATH | AAR | GCN | TGY | 240 |
| Ser | Phe | Ala | Asn | Met | His | Gln | Phe | Asn | Gln | Pro | His | Ile | Lys | Ala | Cys | |
| 65 | | | | 70 | | | | | | 75 | | | | | 80 | |
| TCN | CAY | GTG | ATH | NTN | TTY | GCN | AAY | AAR | NTN | TCN | TAY | ACN | NGN | GAY | GAY | 288 |
| Ser | His | Val | Ile | Leu | Phe | Ala | Asn | Lys | Leu | Ser | Tyr | Thr | Arg | Asp | Asp | |
| | | | | 85 | | | | | 90 | | | | | 95 | | |
| TAY | GAY | GTG | GTN | NTN | TCN | AAR | GCN | GTN | GCN | GAY | AAR | NGN | ATH | ACN | GAR | 336 |
| Tyr | Asp | Val | Val | Leu | Ser | Lys | Ala | Val | Ala | Asp | Lys | Arg | Ile | Thr | Glu | |
| | | | 100 | | | | | 105 | | | | | 110 | | | |
| GAR | CAR | AAR | GAR | GCN | GCN | TTY | GCN | TCN | TTY | AAR | TTY | GTN | GAR | TTG | AAY | 384 |
| Glu | Gln | Lys | Glu | Ala | Ala | Phe | Ala | Ser | Phe | Lys | Phe | Val | Glu | Leu | Asn | |
| | | 115 | | | | | 120 | | | | | 125 | | | | |
| TGY | GAY | GAR | AAY | GGN | GAR | CAY | AAR | GCN | TGG | ACN | AAR | CCN | CAR | GCN | TAY | 432 |
| Cys | Asp | Glu | Asn | Gly | Glu | His | Lys | Ala | Trp | Thr | Lys | Pro | Gln | Ala | Tyr | |
| | 130 | | | | | 135 | | | | | 140 | | | | | |
| NTN | GCN | NTN | GGN | AAY | GCN | NTN | CAY | ACN | NTN | GCN | NGN | NTN | AAY | ATH | GAY | 480 |
| Leu | Ala | Leu | Gly | Asn | Ala | Leu | His | Thr | Leu | Ala | Arg | Leu | Asn | Ile | Asp | |
| 145 | | | | | 150 | | | | | 155 | | | | | 160 | |
| TCN | ACN | ACN | ATG | GAR | GGN | ATH | GAY | CCN | GAR | NTN | TTG | TCN | GAR | ATH | TTY | 528 |
| Ser | Thr | Thr | Met | Glu | Gly | Ile | Asp | Pro | Glu | Leu | Leu | Ser | Glu | Ile | Phe | |
| | | | | 160 | | | | | 170 | | | | | 175 | | |
| GCN | GAY | GAR | NTN | AAR | GGN | TAY | GAR | TGY | CAY | GTN | GCN | NTN | GCN | ATH | GGN | 576 |
| Ala | Asp | Glu | Leu | Lys | Gly | Tyr | Glu | Cys | His | Val | Ala | Leu | Ala | Ile | Gly | |
| | | | 180 | | | | | 185 | | | | | 190 | | | |
| TAY | CAY | CAY | CCN | TCN | GAR | GAY | TAY | AAY | GCN | TCN | TTG | CCN | AAR | TCN | NGN | 624 |
| Tyr | His | His | Pro | Ser | Glu | Asp | Tyr | Asn | Ala | Ser | Leu | Pro | Lys | Ser | Arg | |
| | | 195 | | | | | 200 | | | | | 205 | | | | |
| AAR | GCN | TTY | GAR | GCN | GTN | ATH | ACN | ATH | NTN | TRR | | | | | | 657 |
| Lys | Ala | Phe | Glu | Ala | Val | Ile | Thr | Ile | Leu | | | | | | | |
| | 210 | | | | | 215 | | | | | | | | | | |

( 2 ) INFORMATION FOR SEQ ID NO:2:

( i ) SEQUENCE CHARACTERISTICS:
        ( A ) LENGTH: 657 bases
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL:

( i v ) ANTI-SENSE:

( v ) FRAGMENT TYPE:

( v i ) ORIGINAL SOURCE:
        ( A ) ORGANISM: Vibrio fischeri
        ( B ) STRAIN: ATCC 7744
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:

( A ) NAME/KEY:
( B ) LOCATION:
( C ) IDENTIFICATION METHOD:
( D ) OTHER INFORMATION:

( x ) PUBLICATION INFORMATION:
( A ) AUTHORS:
( B ) TITLE:
( C ) JOURNAL:
( D ) VOLUME:
( E ) ISSUE:
( F ) PAGES:
( G ) DATE:
( H ) DOCUMENT NUMBER:
( I ) FILING DATE:
( J ) PUBLICATION DATE:
( K ) RELEVANT RESIDUES IN SEQ ID NO:

( x i ) SEQUENCE DESCRIPTION: SEQ ID NO:2:

| ATG | ACG | CAT | CCA | ATT | ATT | CAT | GAT | CTT | GAA | AAT | CGT | TAT | ACA | TCA | AAA | 48 |
| Met | Thr | His | Pro | Ile | Ile | His | Asp | Leu | Glu | Asn | Arg | Tyr | Thr | Ser | Lys | |
| 1 | | | | 5 | | | | | 10 | | | | | 15 | | |

| AAA | TAT | GAC | CCA | TCA | AAG | AAA | GTA | TCT | CAA | GAA | GAT | TTA | GCG | GTT | TTG | 96 |
| Lys | Tyr | Asp | Pro | Ser | Lys | Lys | Val | Ser | Gln | Glu | Asp | Leu | Ala | Val | Leu | |
| | | | 20 | | | | | 25 | | | | | 30 | | | |

| CTT | GAG | GCT | CTG | CGT | TTA | TCT | GCT | TCT | TCA | ATT | AAT | TCA | CAG | CCT | TGG | 144 |
| Leu | Glu | Ala | Leu | Arg | Leu | Ser | Ala | Ser | Ser | Ile | Asn | Ser | Gln | Pro | Trp | |
| | | 35 | | | | | 40 | | | | | 45 | | | | |

| AAA | TTC | ATT | GTT | ATT | GAA | TCC | GAT | GCA | GCG | AAG | CAA | GGT | ATG | CAT | GAT | 192 |
| Lys | Phe | Ile | Val | Ile | Glu | Ser | Asp | Ala | Ala | Lys | Gln | Gly | Met | His | Asp | |
| | 50 | | | | | 55 | | | | | 60 | | | | | |

| TCG | TTT | GCA | AAT | ATG | CAT | CAG | TTT | AAT | CAA | CCT | CAC | ATC | AAA | GCG | TGT | 240 |
| Ser | Phe | Ala | Asn | Met | His | Gln | Phe | Asn | Gln | Pro | His | Ile | Lys | Ala | Cys | |
| 65 | | | | 70 | | | | | 75 | | | | | 80 | | |

| TCT | CAT | GTG | ATT | TTA | TTT | GCA | AAT | AAG | CTT | TCG | TAT | ACA | CGA | GAT | GAT | 288 |
| Ser | His | Val | Ile | Leu | Phe | Ala | Asn | Lys | Leu | Ser | Tyr | Thr | Arg | Asp | Asp | |
| | | | | 85 | | | | | 90 | | | | | 95 | | |

| TAT | GAT | GTG | GTT | TTA | TCT | AAA | GCG | GTT | GCT | GAC | AAG | CGT | ATT | ACT | GAA | 336 |
| Tyr | Asp | Val | Val | Leu | Ser | Lys | Ala | Val | Ala | Asp | Lys | Arg | Ile | Thr | Glu | |
| | | | 100 | | | | | 105 | | | | | 110 | | | |

| GAG | CAA | AAA | GAA | GCT | GCT | TTT | GCT | TCG | TTT | AAG | TTT | GTA | GAA | TTG | AAC | 384 |
| Glu | Gln | Lys | Glu | Ala | Ala | Phe | Ala | Ser | Phe | Lys | Phe | Val | Glu | Leu | Asn | |
| | | 115 | | | | | 120 | | | | | 125 | | | | |

| TGT | GAT | GAA | AAT | GGT | GAG | CAT | AAA | GCA | TGG | ACT | AAG | CCT | CAA | GCT | TAT | 432 |
| Cys | Asp | Glu | Asn | Gly | Glu | His | Lys | Ala | Trp | Thr | Lys | Pro | Gln | Ala | Tyr | |
| | 130 | | | | | 135 | | | | | 140 | | | | | |

| TTA | GCT | CTT | GGT | AAT | GCT | CTG | CAT | ACA | TTA | GCT | AGA | CTG | AAC | ATT | GAC | 480 |
| Leu | Ala | Leu | Gly | Asn | Ala | Leu | His | Thr | Leu | Ala | Arg | Leu | Asn | Ile | Asp | |
| 145 | | | | | 150 | | | | | 155 | | | | | 160 | |

| TCA | ACA | ACA | ATG | GAA | GGC | ATT | GAT | CCT | GAA | TTA | TTG | AGT | GAA | ATT | TTT | 528 |
| Ser | Thr | Thr | Met | Glu | Gly | Ile | Asp | Pro | Glu | Leu | Leu | Ser | Glu | Ile | Phe | |
| | | | | 165 | | | | | 170 | | | | | 175 | | |

| GCT | GAT | GAA | TTA | AAA | GGG | TAT | GAA | TGT | CAT | GTT | GCT | TTA | GCC | ATT | GGT | 576 |
| Ala | Asp | Glu | Leu | Lys | Gly | Tyr | Glu | Cys | His | Val | Ala | Leu | Ala | Ile | Gly | |
| | | | 180 | | | | | 185 | | | | | 190 | | | |

| TAT | CAT | CAT | CCA | AGC | GAA | GAT | TAT | AAT | GCC | TCT | TTG | CCT | AAG | TCT | CGT | 624 |
| Tyr | His | His | Pro | Ser | Glu | Asp | Tyr | Asn | Ala | Ser | Leu | Pro | Lys | Ser | Arg | |
| | | 195 | | | | | 200 | | | | | 205 | | | | |

| AAG | GCA | TTT | GAA | GCA | GTA | ATT | ACC | ATC | CTT | TAG | | | | | | 657 |
| Lys | Ala | Phe | Glu | Ala | Val | Ile | Thr | Ile | Leu | | | | | | | |
| | 210 | | | | 215 | | | | | | | | | | | |

( 2 ) INFORMATION FOR SEQ ID NO:3:

(i) SEQUENCE CHARACTERISTICS:
    (A) LENGTH: 929 bases
    (B) TYPE: nucleic acid
    (C) STRANDEDNESS: single
    (D) TOPOLOGY: linear (ii) MOLECULE TYPE: genomic DNA (iii) HYPOTHETICAL:

(iv) ANTI-SENSE:

(v) FRAGMENT TYPE:

(vi) ORIGINAL SOURCE:
    (A) ORGANISM: Vibrio fischeri
    (B) STRAIN: ATCC 7744
    (C) INDIVIDUAL ISOLATE:
    (D) DEVELOPMENTAL STAGE:
    (E) HAPLOTYPE:
    (F) TISSUE TYPE:
    (G) CELL TYPE:
    (H) CELL LINE:
    (I) ORGANELLE:

(vii) IMMEDIATE SOURCE:
    (A) LIBRARY:
    (B) CLONE:

(viii) POSITION IN GENOME:
    (A) CHROMOSOME/SEGMENT:
    (B) MAP POSITION:
    (C) UNITS:

(ix) FEATURE:
    (A) NAME/KEY:
    (B) LOCATION:
    (C) IDENTIFICATION METHOD:
    (D) OTHER INFORMATION:

(x) PUBLICATION INFORMATION:
    (A) AUTHORS:
    (B) TITLE:
    (C) JOURNAL:
    (D) VOLUME:
    (E) ISSUE:
    (F) PAGES:
    (G) DATE:
    (H) DOCUMENT NUMBER:
    (I) FILING DATE:
    (J) PUBLICATION DATE:
    (K) RELEVANT RESIDUES IN SEQ ID NO:

(xi) SEQUENCE DESCRIPTION: SEQ ID NO:3:

```
TGTCACATAT GGCAAATTAA ATATTGAGTA TGCCTTGCTT GTTGACATCA TAAGTTGTGC        60

AGACAAGAAT GTCTGTGGAT TAAAATTTCA CAAGTAAGGT TTATTATT ATG ACG CAT       117
                                                     Met Thr His
                                                      1

CCA ATT ATT CAT GAT CTT GAA AAT CGT TAT ACA TCA AAA AAA TAT GAC        165
Pro Ile Ile His Asp Leu Glu Asn Arg Tyr Thr Ser Lys Lys Tyr Asp
     5              10                  15

CCA TCA AAG AAA GTA TCT CAA GAA GAT TTA GCG GTT TTG CTT GAG GCT        213
Pro Ser Lys Lys Val Ser Gln Glu Asp Leu Ala Val Leu Leu Glu Ala
 20              25                  30                  35

CTG CGT TTA TCT GCT TCT TCA ATT AAT TCA CAG CCT TGG AAA TTC ATT        261
Leu Arg Leu Ser Ala Ser Ser Ile Asn Ser Gln Pro Trp Lys Phe Ile
             40                  45                  50

GTT ATT GAA TCC GAT GCA GCG AAG CAA GGT ATG CAT GAT TCG TTT GCA        309
Val Ile Glu Ser Asp Ala Ala Lys Gln Gly Met His Asp Ser Phe Ala
             55                  60                  65

AAT ATG CAT CAG TTT AAT CAA CCT CAC ATC AAA GCG TGT TCT CAT GTG        357
Asn Met His Gln Phe Asn Gln Pro His Ile Lys Ala Cys Ser His Val
```

```
                        70                              75                                  80
ATT  TTA  TTT  GCA  AAT  AAG  CTT  TCG  TAT  ACA  CGA  GAT  GAT  TAT  GAT  GTG              405
Ile  Leu  Phe  Ala  Asn  Lys  Leu  Ser  Tyr  Thr  Arg  Asp  Asp  Tyr  Asp  Val
     85                            90                      95

GTT  TTA  TCT  AAA  GCG  GTT  GCT  GAC  AAG  CGT  ATT  ACT  GAA  GAG  CAA  AAA              453
Val  Leu  Ser  Lys  Ala  Val  Ala  Asp  Lys  Arg  Ile  Thr  Glu  Glu  Gln  Lys
100                      105                      110                           115

GAA  GCT  GCT  TTT  GCT  TCG  TTT  AAG  TTT  GTA  GAA  TTG  AAC  TGT  GAT  GAA              501
Glu  Ala  Ala  Phe  Ala  Ser  Phe  Lys  Phe  Val  Glu  Leu  Asn  Cys  Asp  Glu
                    120                      125                      130

AAT  GGT  GAG  CAT  AAA  GCA  TGG  ACT  AAG  CCT  CAA  GCT  TAT  TTA  GCT  CTT              549
Asn  Gly  Glu  His  Lys  Ala  Trp  Thr  Lys  Pro  Gln  Ala  Tyr  Leu  Ala  Leu
               135                      140                      145

GGT  AAT  GCT  CTG  CAT  ACA  TTA  GCT  AGA  CTG  AAC  ATT  GAC  TCA  ACA  ACA              597
Gly  Asn  Ala  Leu  His  Thr  Leu  Ala  Arg  Leu  Asn  Ile  Asp  Ser  Thr  Thr
          150                      155                      160

ATG  GAA  GGC  ATT  GAT  CCT  GAA  TTA  TTG  AGT  GAA  ATT  TTT  GCT  GAT  GAA              645
Met  Glu  Gly  Ile  Asp  Pro  Glu  Leu  Leu  Ser  Glu  Ile  Phe  Ala  Asp  Glu
     165                      170                      175

TTA  AAA  GGG  TAT  GAA  TGT  CAT  GTT  GCT  TTA  GCC  ATT  GGT  TAT  CAT  CAT              693
Leu  Lys  Gly  Tyr  Glu  Cys  His  Val  Ala  Leu  Ala  Ile  Gly  Tyr  His  His
180                      185                      190                           195

CCA  AGC  GAA  GAT  TAT  AAT  GCC  TCT  TTG  CCT  AAG  TCT  CGT  AAG  GCA  TTT              741
Pro  Ser  Glu  Asp  Tyr  Asn  Ala  Ser  Leu  Pro  Lys  Ser  Arg  Lys  Ala  Phe
                    200                      205                      210

GAA  GCA  GTA  ATT  ACC  ATC  CTT                                                            762
Glu  Ala  Val  Ile  Thr  Ile  Leu
               215

TAGATTCTTA  ATGTTTGAGA  TGAAGAAAAG  CCAGCGATTT  AGCTGTGCTT  TGTTTGTGCA                       822

AAAATGTTCC  TAATGGCGTA  TTACTACGGT  AGGAAGTCTA  TTTAAAGTTT  CTTTTACTCT                       882

TTGGTATTAA  TTGTCAATTA  CGCGGAAATC  ATTATCTAAC  TAGGCCT                                      929
```

( 2 ) INFORMATION FOR SEQ ID NO:4:

( i ) SEQUENCE CHARACTERISTICS:
        ( A ) LENGTH: 218 amino acids
        ( B ) TYPE: amino acid
        ( C ) STRANDEDNESS: single
        ( D ) TOPOLOGY: linear ( i i ) MOLECULE TYPE:

( i i i ) HYPOTHETICAL:

( i v ) ANTI-SENSE:

( v ) FRAGMENT TYPE:

( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:

(C) UNITS:

(ix) FEATURE:
(A) NAME/KEY:
(B) LOCATION:
(C) IDENTIFICATION METHOD:
(D) OTHER INFORMATION:

(x) PUBLICATION INFORMATION:
(A) AUTHORS:
(B) TITLE:
(C) JOURNAL:
(D) VOLUME:
(E) ISSUE:
(F) PAGES:
(G) DATE:
(H) DOCUMENT NUMBER:
(I) FILING DATE:
(J) PUBLICATION DATE:
(K) RELEVANT RESIDUES IN SEQ ID NO:

(xi) SEQUENCE DESCRIPTION: SEQ ID NO:4:

| Met | Thr | His | Pro | Ile | Ile | His | Asp | Leu | Glu | Asn | Arg | Tyr | Thr | Ser | Lys |
|---|---|---|---|---|---|---|---|---|---|---|---|---|---|---|---|
| 1 | | | | 5 | | | | | 10 | | | | | 15 | |

| Lys | Tyr | Asp | Pro | Ser | Lys | Lys | Val | Ser | Gln | Glu | Asp | Leu | Ala | Val | Leu |
|---|---|---|---|---|---|---|---|---|---|---|---|---|---|---|---|
| | | | 20 | | | | 25 | | | | | 30 | | | |

| Leu | Glu | Ala | Leu | Arg | Leu | Ser | Ala | Ser | Ser | Ile | Asn | Ser | Gln | Pro | Trp |
|---|---|---|---|---|---|---|---|---|---|---|---|---|---|---|---|
| | | 35 | | | | | 40 | | | | | 45 | | | |

| Lys | Phe | Ile | Val | Ile | Glu | Ser | Asp | Ala | Ala | Lys | Gln | Gly | Met | His | Asp |
|---|---|---|---|---|---|---|---|---|---|---|---|---|---|---|---|
| | 50 | | | | | 55 | | | | | 60 | | | | |

| Ser | Phe | Ala | Asn | Met | His | Gln | Phe | Asn | Gln | Pro | His | Ile | Lys | Ala | Cys |
|---|---|---|---|---|---|---|---|---|---|---|---|---|---|---|---|
| 65 | | | | | 70 | | | | | 75 | | | | | 80 |

| Ser | His | Val | Ile | Leu | Phe | Ala | Asn | Lys | Leu | Ser | Tyr | Thr | Arg | Asp | Asp |
|---|---|---|---|---|---|---|---|---|---|---|---|---|---|---|---|
| | | | | 85 | | | | | 90 | | | | | 95 | |

| Tyr | Asp | Val | Val | Leu | Ser | Lys | Ala | Val | Ala | Asp | Lys | Arg | Ile | Thr | Glu |
|---|---|---|---|---|---|---|---|---|---|---|---|---|---|---|---|
| | | | 100 | | | | | 105 | | | | | 110 | | |

| Glu | Gln | Lys | Glu | Ala | Ala | Phe | Ala | Ser | Phe | Lys | Phe | Val | Glu | Leu | Asn |
|---|---|---|---|---|---|---|---|---|---|---|---|---|---|---|---|
| | | 115 | | | | | 120 | | | | | 125 | | | |

| Cys | Asp | Glu | Asn | Gly | Glu | His | Lys | Ala | Trp | Thr | Lys | Pro | Gln | Ala | Tyr |
|---|---|---|---|---|---|---|---|---|---|---|---|---|---|---|---|
| | 130 | | | | | 135 | | | | | 140 | | | | |

| Leu | Ala | Leu | Gly | Asn | Ala | Leu | His | Thr | Leu | Ala | Arg | Leu | Asn | Ile | Asp |
|---|---|---|---|---|---|---|---|---|---|---|---|---|---|---|---|
| 145 | | | | | 150 | | | | | 155 | | | | | 160 |

| Ser | Thr | Thr | Met | Glu | Gly | Ile | Asp | Pro | Glu | Leu | Leu | Ser | Glu | Ile | Phe |
|---|---|---|---|---|---|---|---|---|---|---|---|---|---|---|---|
| | | | | 165 | | | | | 170 | | | | | 175 | |

| Ala | Asp | Glu | Leu | Lys | Gly | Tyr | Glu | Cys | His | Val | Ala | Leu | Ala | Ile | Gly |
|---|---|---|---|---|---|---|---|---|---|---|---|---|---|---|---|
| | | | 180 | | | | | 185 | | | | | 190 | | |

| Tyr | His | His | Pro | Ser | Glu | Asp | Tyr | Asn | Ala | Ser | Leu | Pro | Lys | Ser | Arg |
|---|---|---|---|---|---|---|---|---|---|---|---|---|---|---|---|
| | | 195 | | | | | 200 | | | | | 205 | | | |

| Lys | Ala | Phe | Glu | Ala | Val | Ile | Thr | Ile | Leu |
|---|---|---|---|---|---|---|---|---|---|
| | 210 | | | | | 215 | | | |

(2) INFORMATION FOR SEQ ID NO:5:

(i) SEQUENCE CHARACTERISTICS:
(A) LENGTH: 24 amino acids
(B) TYPE: amino acid
(C) STRANDEDNESS: single
(D) TOPOLOGY: linear (ii) MOLECULE TYPE:

(iii) HYPOTHETICAL:

(iv) ANTI-SENSE:

(v) FRAGMENT TYPE:

(vi) ORIGINAL SOURCE:
    (A) ORGANISM:
    (B) STRAIN:
    (C) INDIVIDUAL ISOLATE:
    (D) DEVELOPMENTAL STAGE:
    (E) HAPLOTYPE:
    (F) TISSUE TYPE:
    (G) CELL TYPE:
    (H) CELL LINE:
    (I) ORGANELLE:

(vii) IMMEDIATE SOURCE:
    (A) LIBRARY:
    (B) CLONE:

(viii) POSITION IN GENOME:
    (A) CHROMOSOME/SEGMENT:
    (B) MAP POSITION:
    (C) UNITS:

(ix) FEATURE:
    (A) NAME/KEY:
    (B) LOCATION:
    (C) IDENTIFICATION METHOD:
    (D) OTHER INFORMATION:

(x) PUBLICATION INFORMATION:
    (A) AUTHORS:
    (B) TITLE:
    (C) JOURNAL:
    (D) VOLUME:
    (E) ISSUE:
    (F) PAGES:
    (G) DATE:
    (H) DOCUMENT NUMBER:
    (I) FILING DATE:
    (J) PUBLICATION DATE:
    (K) RELEVANT RESIDUES IN SEQ ID NO:

(xi) SEQUENCE DESCRIPTION: SEQ ID NO:5:

```
Met Thr His Pro Ile Ile His Asp Leu Glu Asn Arg Tyr
 1               5                  10
Thr Ser Lys Lys Tyr Asp Pro Ser Lys Lys Val
        15              20
```